United States Patent [19]

Crystal

[11] Patent Number: 5,238,683
[45] Date of Patent: Aug. 24, 1993

[54] AEROSOL PREPARATION OF GLUTATHIONE AND A METHOD FOR AUGMENTING GLUTATHIONE LEVEL IN LUNGS

[75] Inventor: Ronald G. Crystal, Potomac, Md.

[73] Assignee: The United States of America as represented by the Department of Health and Human Services, Washington, D.C.

[21] Appl. No.: 441,521

[22] Filed: Nov. 24, 1989

[51] Int. Cl.$^5$ .................. A61F 13/00; A61K 9/12; A61K 37/02
[52] U.S. Cl. .................... 424/434; 424/43; 514/2; 514/18; 514/21; 530/331; 530/332
[58] Field of Search ............... 424/47, 489, 490, 434, 424/43; 128/200.14; 514/18, 21, 2; 530/331

[56] References Cited

U.S. PATENT DOCUMENTS

| | | | |
|---|---|---|---|
| 3,984,569 | 10/1976 | Kalopissis et al. | 514/562 |
| 4,424,216 | 1/1984 | Cerami | 424/211 |
| 4,710,489 | 12/1987 | Meister | 514/18 |
| 4,732,901 | 3/1988 | Buckle | 514/461 |
| 4,761,399 | 8/1988 | Pilotto et al. | 514/19 |

OTHER PUBLICATIONS

Buhl et al, 1990 Clin. Res. 38(2):596A.
Roum et al, 1990. Am. Rev. Respir. Dis. 141(4):A87.
Borok et al, 1990. Am. Rev. Respir. Dis. 141(4):A320.
Roum et al, 1990. Clin. Res. 38(2) 440A.

Primary Examiner—Thurman K. Page
Assistant Examiner—G. S. Kishore
Attorney, Agent, or Firm—Cushman, Darby & Cushman

[57] ABSTRACT

An aerosol preparation of reduced glutathione (GSH) is provided to augment the level of GSH in the lungs. Treatment of pulmonary conditions, where reduced level of GSH is found, by the aerosol preparation of the present invention is taught.

5 Claims, 5 Drawing Sheets

TOTAL GLUTATHIONE THAT IS
GSH (%)

BEFORE    AFTER

AEROSOLIZATION

FIG. 3

AEROSOL PREPARATION OF GLUTATHIONE AND A METHOD FOR AUGMENTING GLUTATHIONE LEVEL IN LUNGS

The present invention is related generally to the control and treatment of pulmonary disorders. More particularly, the present invention is related to combating pulmonary dysfunction, disease or disorder by augmenting reduced glutathione (GSH) levels in the tissues of the lower respiratory tract by direct aerosol administration of glutathione through inhalation.

BACKGROUND OF THE INVENTION

In the lung, GSH is present in high concentrations in the epithelial lining fluid (ELF) of the lower respiratory tract, with normal levels in human ELF being more than 40-fold greater than that in plasma. As such, ELF GSH is a major component of the antioxidant screen that protects the pulmonary epithelium from oxidants released by inflammatory cells as well as inhaled oxidants. In addition, ELF GSH helps maintain the normal function of the immune components of the pulmonary epithelial host defense system. However, in certain conditions, such as idiopathic pulmonary fibrosis and AIDS patients, there is found to be a substantial ELF GSH deficiency. A problem in augmenting GSH levels in the lungs is that oral administration of GSH does not achieve significant elevation of GSH level in the lungs and intravenous administration of GSH is associated with a very short plasma half-life of the molecule.

SUMMARY OF THE INVENTION

It is, therefore, an object of the present invention to provide a novel, efficacious method of delivering GSH in the lungs.

It is a further object of the present invention to provide a substantially non-toxic, aerosol composition of GSH for direct administration to human lungs.

It is another object of the present invention to provide a method of combating pulmonary dysfunction, disorder or disease where increased level of GSH is deemed beneficial by directly administering aerosol GSH to the lungs.

Various other objects and advantages of the present invention will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein:

FIG. 3 is an evaluation of the effect of aerosolization on glutathione. The output of the aerosol generator was collected in phosphate buffered saline. Shown is the proportion of total glutathione in the reduced form for the preaerosol glutathione ("before") and the aerosol generated with room air ("after"). Each data point represents the average of triplicate determinations.

DETAILED DESCRIPTION OF THE INVENTION

Figure 1:
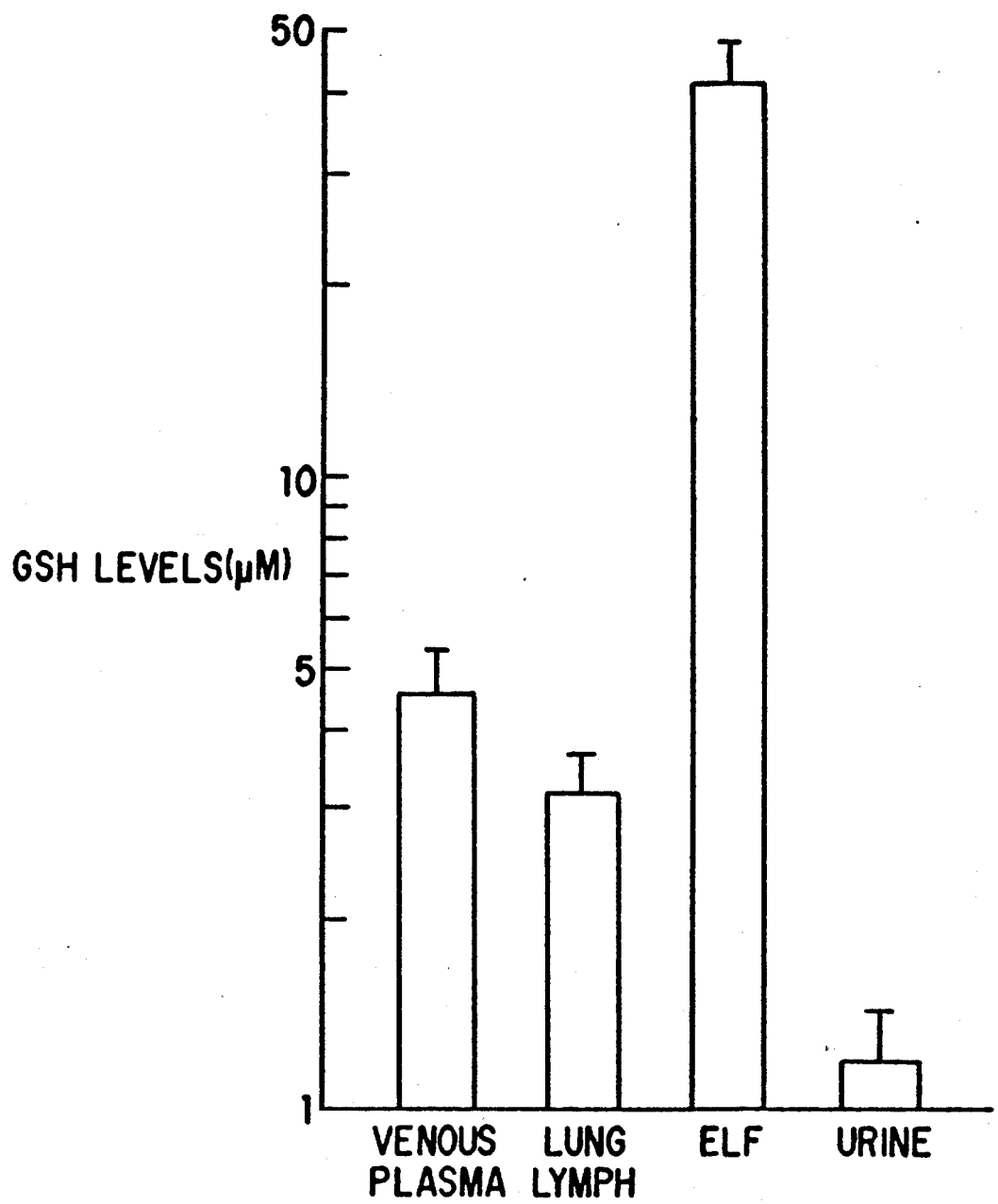
FIG. 1 shows the baseline glutathione levels in sheep. Shown are the concentrations of reduced glutathione (GSH) in venous plasma, lung lymph, epithelial lining fluid, and urine. The data represents the averaged duplicate values from 23 sheep.
Figure 2A:
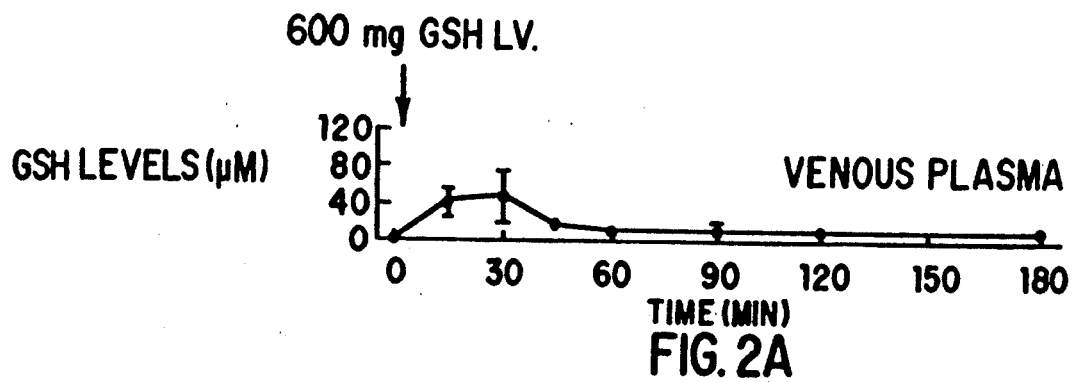
FIG. 2 shows the reduced glutathione (GSH) levels in sheep following intravenous administration of 600 mg GSH. The GSH concentrations in venous plasma (FIG. 2A), lung lymph (FIG. 2B), lung epithelial lining fluid (ELF), (FIG. 2C) and urine, (FIG. 2D) were evaluated before and at intervals after intravenous GSH administration. Each data point represents the average of duplicate determinations from 11 sheep.
Figure 2B:
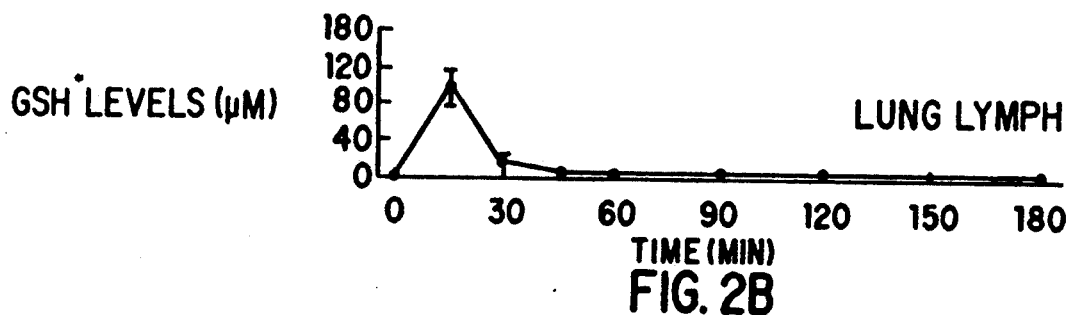
Figure 2C:
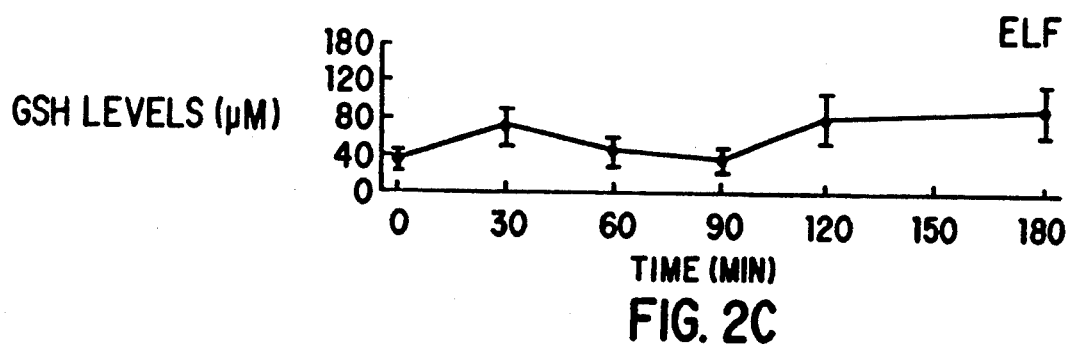
Figure 2D:
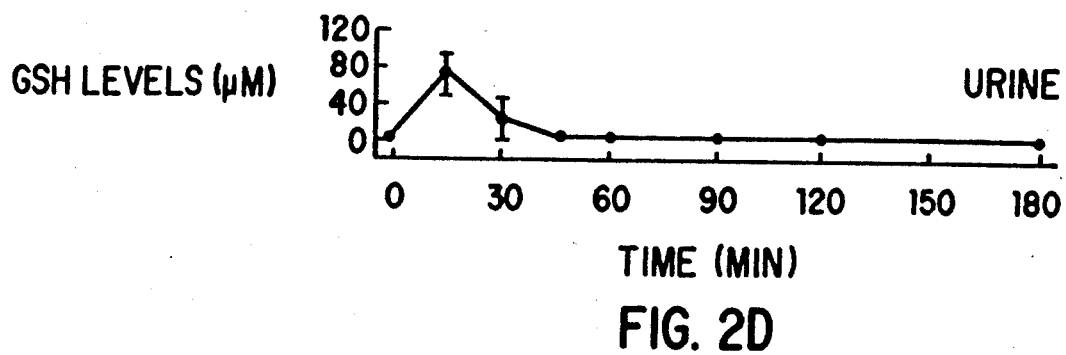
Figure 4A:
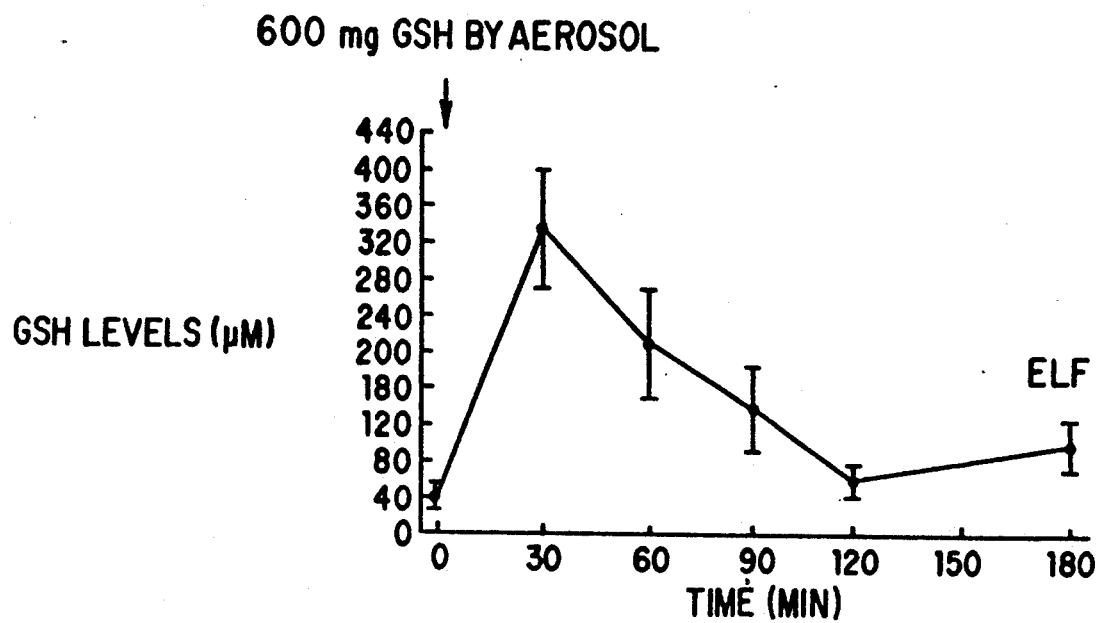
FIG. 4 shows reduced glutathione (GSH) levels in sheep following aerosol administration of 600 mg GSH. The concentrations of GSH in lung epithelial lining fluid (ELF) FIG. 4A, lung lymph (FIG. 4B), venous plasma (FIG. 4C), and urine (FIG. 4D), were evaluated before and at intervals after aerosol GSH administration. Each data point represents the average of duplicate determinations from 12 sheep.
Figure 4B:
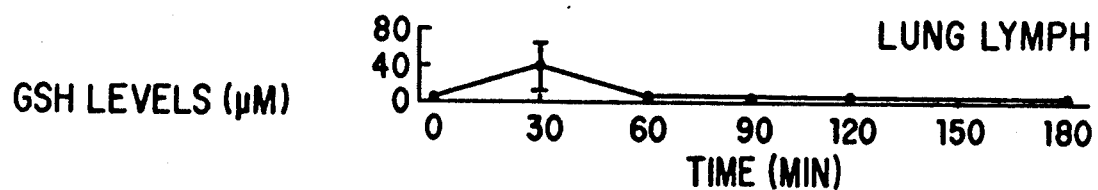
Figure 4C:
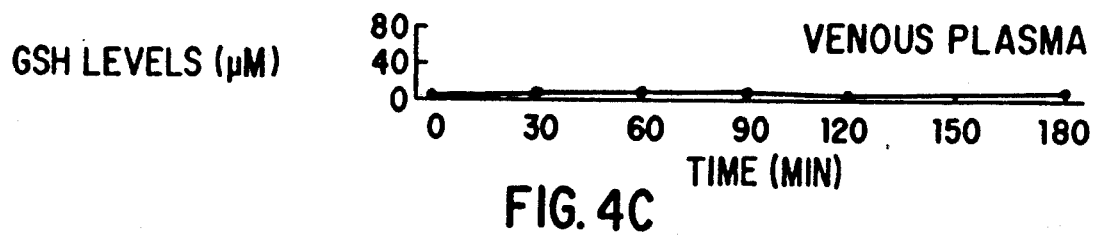
Figure 4D:
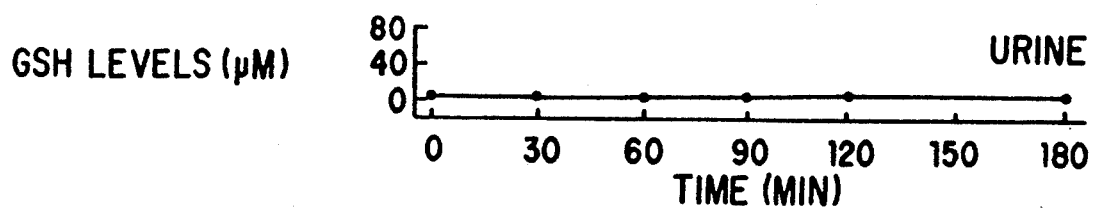

The above and various other objects and advantages of the present invention are achieved by a non-toxic aerosol composition of GSH suitable for direct administration to human lungs through inhalation. An aerosol composition of GSH comprises an effective amount of GSH in a pharmaceutically acceptable carrier in the form of an aerosol suitable for safe administration to the lungs by inhalation.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only and not limiting.

The term "aerosol" as used herein means droplets of a liquid suspended in air. It is understood that the droplet size would be appropriate for deposition of the aerosol in the upper and lower respiratory tract as deemed necessary for the clinical condition for which the aerosol containing GSH is to be used.

MATERIALS AND METHODS

Glutathione Preparation

The reduced form of glutathione was obtained as a free acid (tissue culture grade; Sigma) and stored at 4° C. The percentage of reduced glutathione in this preparation prior to each experiment was constantly >96% (vide infra).

Experimental Model

Female mixed breed sheep (n=23; 33+1 kg) were anesthetized with intravenous sodium thiopental. Intravenous catheters were placed in a jugular vein and in a vein of the hind limb, and a catheter was inserted into the bladder. The trachea was intubated with a cuffed endotracheal tube attached to a positive pressure ventilator. Animals were ventilated at a tidal volume of 12 ml/kg body weight with 5 cm of $H_2O$ positive endexpiratory pressure at a rate of 16/min. Electrocardiogram and inspiratory pressure were monitored throughout the study.. Anesthesia was maintained with 1.0-1.5% fluothane and 50% oxygen. Lung lymph was collected from the caudal efferent lymphatic duct cannulated with a heparinized silastic catheter by the technique of Staub et al (1975, *J. Surg. Res.* 19, 315-320), a method that permits selective sampling of lung lymph draining the pulmonary interstitium. Lower respiratory tract ELF was obtained by bronchoalveolar lavage through a fiberoptic bronchoscope (length: 1 m, external diameter: 5.3 mm; Machida) using a single 50 ml aliquot of 0.9% NaCl. Blood samples were obtained from the catheter in the jugular vein, and urine samples were obtained from the bladder catheter. Venous plasma, lung lymph, ELF and urine were obtained before GSH administration, and at intervals up to 180 min following intravenous administration or aerosolization of 600 mg of GSH. A total of 23 sheep were evaluated; the number of sheep used for each set of experiments are indicated with the data. All intravenous and aerosol studies were performed with the chest closed and the animal in the prone position. After baseline bronchoalveolar lavage fluid, blood, lung lymph and urine samples were obtained, 600 mg glutathione in 4 ml of saline was administered either intravenously into a vein of the hind leg or by aerosol into the inspiratory limb of the ventilation circuit over a 25 min period. Bronchoalveolar lavage fluid, blood, lymph, and urine samples were then obtained at various intervals over a 3 hr period. Lavage samples at different time points were obtained from different sites. All measurements were carried out in duplicate. Lymph, blood, and urine values are referenced to the volumes of the fluids analyzed. Lower respiratory tract values were referenced to the volume of epithelial lining fluid recovered as assessed by the urea method (Rennard et al, 1986, *J. Appl. Physiol.* 60, 532-538). All data is presented as mean±standard error of the mean; all statistical comparisons were made using the two-tailed Student's t-test.

Aerosol Generating System

Reduced glutathione was put into a form capable of reaching the lower respiratory tract with a nebulizer (Ultravent, Mallinckrodt) capable of generating aerosol droplets of a size appropriate for deposition in the alveolar regions (Hubbard et al, 1989, *Proc. Natl. Acad. Sci. USA* 86, 680-684). To generate the aerosol containing the reduced glutathione, 4 ml of a solution of GSH at a concentration of 150 mg/ml in 0.9% NaCl was placed in the reservoir of the nebulizer, and the nebulizer was driven at 40 psi with compressed air. The size distribution of aerosol droplets determined by laser particle-size analysis demonstrated a mass median aerodynamic diameter of the droplets of 2.8 $\mu$m with a geometric standard deviation of 1.3 $\mu$m. The relative proportion of the GSH preparation that remained in the reduced form was evaluated by collecting the aerosolized droplets in phosphate buffered saline, pH 7.4, as previously described (Hubbard et al, supra).

Glutathione Levels and Form

Glutathione levels in venous plasma, lung lymph, bronchoalveolar lavage fluid and urine were quantified with minor modifications of standard methods (Cantin et al, 1987, *J. Appl. Physiol.* 63, 152-157; Adams et al, 1983, *J. Pharmacol. Exp. Ther.* 227, 749-754; Sies et al, 1984, *Methods Enzymol* 105, 445-451; Martensson et al, 1989, *Proc. Natl. Acad. Sci. USA* 86, 5296-5300). In brief, to determine the total glutathione levels [i.e., reduced glutathione+glutathione disulfide (GSSG)], the various fluids were mixed with an equal amount of 10 mM 5,5'-dithiobis(2-nitrobenzoic acid) (DTNB) in 0.1M potassium phosphate, pH 7.5, containing 17.5 mM ethylenediaminetetraacetic acid (EDTA). The samples were centrifuged (2000 g, 10 min), and aliquots (50 $\mu$l) of the supernatants were added to cuvettes containing 0.5 U of GSSG reductase in 0.1M potassium phosphate, pH 7.5, containing 5 mM EDTA. After incubation for 1 min, 25° C., the assay reaction was started by adding 220 nM of reduced $\beta$-nicotinamide adenine dinucleotide phosphate (NADPH) in 0.1M potassium phosphate, pH 7.5, containing 5 mM EDTA in a final volume of 1 ml. The rate of reduction of DTNB was recorded spectrophotometrically at a wavelength of 412 nm (Beckman DU-70 spectrophotometer). Determination of the total gluthathione concentration was based on standard curves generated from known concentrations of GSSG (0.125 to 4 $\mu$M) in phosphate buffered saline, pH 7.4.

To quantify glutathione disulfide, the various fluids were mixed, immediately after recovery, with an equal volume of 10 mM N-ethylmaleimide (NEM) in 0.1M potassium phosphate, pH 6.5, containing 17.5 mM EDTA. The samples were then centrifuged at 2000 g, 10 min, and 250 $\mu$l of the supernatant was passed through a SEP-PAK C18 cartridge (Waters Associates) that had been washed with 3 ml methanol followed by 3 ml distilled water, and the effluent was collected. GSSG was eluted from the column with 1 ml of 0.1M potassium phosphate, pH 7.5, containing 5 mM EDTA. An aliquot (750 $\mu$l) of the combined effluent and eluate was mixed with 250 $\mu$l 0.1M potassium phosphate, pH 7.5, containing 5 mM EDTA, 800 $\mu$M DTNB, 2 U/ml glutathione reductase, and 1 mM NADPH, and the rate of reduction of DTNB was recorded spectrophotometrically at 412 nm. Standard curves were derived from dilutions of known concentrations of GSSG (0.125 to 4 $\mu$M) that had been mixed with 10 mM NEM and chromatographed with SEP-PAK C18 cartridges as described above. If values above the range of the standard curve were observed, parallel runs of samples diluted with 0.9% NaCl were performed. The amount of GSH was obtained by subtracting the amount of GSSG from the total glutathione levels. For both the total glutathione and GSSG assays, standard curves generated in the various fluids were parallel, i.e., the values from all fluids were comparable.

RESULTS

Baseline Glutathione Levels in Sheep

The reduced glutathione levels in venous plasma and in lung lymph were in a similar range, although the plasma levels were slightly higher (p>0.1; FIG. 1). Urine levels were much lower. Strikingly, as in humans (Cantin et al, supra; Buhl et al, 1989, *Lancet* II, 8675; Cantin et al, 1989, *Am. Rev. Respir. Dis.* 139, 370-372), lung epithelial lining fluid GSH concentrations were several-fold greater than those in plasma or lung lymph. In both plasma and lung lymph, GSH accounted for >95% of the total glutathione (plasma 97±2% reduced; lymph 95±3% reduced). In ELF 75±4% of the baseline total glutathione was in the reduced form, while in urine 59±6% was in the reduced form.

Intravenous Administration of Glutathione

To evaluate the intravenous route as a possible way of augmenting GSH levels of lung epithelial lining fluid, single doses of 600 mg GSH were given intravenously to sheep. Levels of GSH in plasma increased following the injection, but returned to baseline by 45 min ($p<0.05$, 15 min compared to baseline, all other values $p>0.1$; FIG. 2). Some GSH diffused into the lung, transiently raising lung lymph levels ($p<0.05$, 15 min compared to baseline), but like the plasma GSH, by 30 min the values went to baseline ($p>0.1$, all times other than 15 min). Although the average lung epithelial lining fluid values were variable, they did not change significantly during the observation period ($p>0.1$, all comparisons to baseline values). As expected, urine excretion was rapid with high levels at 15 min ($p<0.02$, compared to baseline). This was also transient, with baseline values thereafter ($p>0.1$). Evaluation of the total glutathione levels in plasma, lymph, ELF and urine demonstrated a pattern similar to that of reduced glutathione (data not shown). Together, these observations indicate that the intravenous route is not an efficacious means of delivering GSH to the epithelial surface of the lung.

Effect of Aerosolization of GSH

To use aerosolization to deliver GSH to the lower respiratory tract, at least three main criteria must be fulfilled. First, the solution of GSH must be placed into an aerosol composed of droplets of an optimal size for deposition on the alveolar surface. This requirement was fulfilled with the Ultravent nebulizer used in these studies, but can be achieved with other nebulizers or the like which produce aerosols with similar characteristics as is well known to one of ordinary skill in the art. Second, the aerosol should not alter the GSH, i.e., it must remain reduced and therefore functional. Third, the aerosolic composition should be non-toxic, that is suitable for human use. In vitro evaluation of the aerosolized GSH revealed that the aerosolization process itself did not alter the structure of the glutathione molecule. In this regard, the total glutathione in the pre-aerosol preparations contained $98.2\pm0.1\%$ glutathione in the reduced form, while the post-aerosol glutathione in the collected aerosolized droplets had $97.0\pm0.6\%$ in the reduced form ($p>0.1$; FIG. 3). Together, these observations demonstrate that the aerosol was composed of fully functioning reduced glutathione within droplets of an optimal size for reaching the alveolar regions of the lung.

Aerosol Administration of Glutathione

Single doses of 600 mg reduced glutathione in 4 ml of 0.9% NaCl given by aerosol over 25 min to sheep (n=12) increased the GSH levels in the epithelial lining fluid of the lower respiratory tract over 7-fold within 30 minutes ($p<0.001$, pre-aerosol compared to 30 min post-aerosol; FIG. 4). ELF GSH levels remained greater than baseline for up to 2 hr ($p<0.01$, 60 min and 90 min post-aerosol, both comparisons to baseline). Levels in lung lymph increased only transiently at 30 min, but were not significantly different from the baseline ($p>0.1$) and levels in venous plasma and urine did not change significantly following aerosolization ($p>0.1$, all comparisons to baseline). As a control, only saline was aerosolized; GSH levels in ELF remained unchanged from baseline over a 3 hr period ($p>0.1$, all comparisons).

At each time point where ELF GSH levels were significantly above the baseline, evaluation of the total glutathione levels in ELF demonstrated higher levels than reduced glutathione. For example, at 30 min the reduced glutathione levels in ELF were $65\pm7\%$ that of the total levels ($p<0.001$). Overall, at 60, 90 and 120 min, reduced glutathione levels were 62 to 65% that of the total levels ($p<0.005$, all comparisons). Since the aerosolization process itself did not alter the relative proportions of GSH from that in the pre-aerosol preparation (FIG. 3), yet a proportion of the recovered GSH was not reduced, it is likely that the GSH encountered an oxidant burden when impacting on the epithelial surface of the sheep lung. However, independent of this observation, it is clear beyond doubt that the aerosolization of GSH results in a marked augmentation of GSH levels in ELF (FIG. 4).

Together, these data demonstrate that aerosolization of glutathione is a feasible and effective method for targeting reduced glutathione to the ELF of the lower respiratory tract. In regards to the safety of the therapy, the mean and peak inspiratory pressures remained stable throughout the procedure. Aerosolization of GSH did not result in inflammation of the lower respiratory tract, as judged by visual inspection of the mucous membranes of the respiratory tract. Further, there was no apparent "leak" of the epithelial barrier, as determined by measurements of ELF volumes of pre- and post-aerosol bronchial lavage fluids ($p>0.1$, all comparisons to baseline values).

STUDY OF AEROSOLIZED GLUTATHIONE IN HUMANS

It has been found that in such patients as with idiopathic pulmonary fibrosis (IPF), the ELF glutathione concentration is approximately four-fold lower suggesting that in the context of the increased oxidant burden found in IPF, there is a marked oxidant-antioxidant deficiency at the alveolar surface (Cantin et al, supra). Similarly, GSH deficiency has been observed in the ELF of HIV-seropositive individuals. There is an inflammatory cell-derived increased oxidant burden together with a deficient antioxidant screen of the epithelial surface of the lower respiratory tract in patients with IPF and in HIV-seropositive individuals. Together, these processes most likely play a role in the epithelial damage seen in these patients. Other conditions where administration of the increased level of GSH in the lungs may be deemed desirable include cystic fibrosis, acute and chronic bronchitis, adult respiratory distress syndrome, all forms of lung infection including bacterial and viral pneumonias, opportunistic infections, mycoplasma, Legionella, mycobacteria and fungal infections and the like.

The present study was undertaken with the following main objectives:

1. To demonstrate the safety of the administration of increasing amounts of aerosolized GSH to patients with idiopathic pulmonary fibrosis or individuals seropositive for the HIV virus, monitoring history and physical examination, chemistry, hematology and coagulation profiles, and pulmonary function and using bronchoalveolar lavage to evaluate any abnormal inflammatory reaction in the lung.
2. To determine that a dose of glutathione that likely will be clinically efficacious for those disorders can be safely administered to the lung by aerosol and evaluate the subsequent bioavailability of the GSH in the lower respiratory tract using bronchoalveolar lavage.

3. To evaluate the half-life of administered glutathione in epithelial lining fluid and the functionality of the administered GSH as an anti-oxidant after aerosol administration.

Patient Selection:
A. Subjects
1. Criteria for selection of study patients
   a. Patients determined to have
      (1) idiopathic pulmonary fibrosis as defined by standard criteria (Crystal et al, Ann Intern Med 1976, 85: 769-88) including mild to moderate restrictive lung physiology with an open lung biopsy compatible with IPF; or
      (2) HIV-seropositivity without evidence of opportunistic infections or Kaposi's sarcoma.
   b. All study subjects to be non-smokers, i.e., never smoked or stopped smoking more than two years prior to study.
   c. Patients of either sex shall be eligible; the minimum age will be 18 years.
   d. No history of recent upper respiratory infection.
B. Medications
1. Patients on corticosteroids or cyclophosphamide for therapy of IPF will remain on therapy. HIV seropositive patients on AZT will remain on therapy. Patients receiving any other drug by aerosol will be excluded.

Study Design:
A. Part I—Evaluation of Increasing Doses of GSH.

Each patient to receive a single aerosol of reduced glutathione every 24 hr for four successive doses at four successive dose levels (in the absence of unacceptable toxicity).

The schedule of dose administrations is as follows.

| Day of Study | Dose |
| --- | --- |
| 1 | 10 mg |
| 2 | 50 mg |
| 3 | 200 mg |
| 4 | 600 mg |

It should be noted, however, that the dosage can be adjusted to any level of GSH which is tolerated without substantial adverse effect by the patient. Thus, dosages up to 2,500 mg or higher could be considered by the physician if such high levels would produce the desirable result in the patient.

All patients will begin treatment at 10 mg and will be dose escalated in each successive treatment if not accompanied by Grade II toxicity or Grade III toxicity. Up to 2 patients will be treated simultaneously. If toxicity occurs in either individual, four additional patients will be treated at that dose level before further dose escalation can occur. If toxicity occurs in a second individual, no escalation in dose will occur until the source of the toxicity is determined and removed.

B. Part II—Evaluation of Bioavailability of GSH.

Each patient will receive 600 mg or the maximum tolerated dose 12 hr apart for 6 doses.

C. Administration of GSH

Each patient will receive aerosolized GSH at a particular dosage. A physician will be in attendance during aerosol administration to manage any adverse reaction.

Direction for the administration of Aerosolized Glutathione

A. Dilution Vehicle
Dilution vehicle is sterile 0.9% sodium chloride.
B. Dosing Instructions
Vials will be reconstituted immediately before use and any excess will be discarded. Separate vials of glutathione will be allocated per patient dose.

In each case the desired dose will be 4 ml of the reconstituted solution as follows:
10 mg: reconstituted 50 mg/vial with 20 ml
50 mg: reconstituted 50 mg/vial with 4 ml
200 mg: reconstituted 600 mg/vial with 12 ml
600 mg: reconstituted 600 mg/vial with 4 ml Following reconstitution, 4 ml of the solution will be placed in the reservoir of a pneumatic aerosol generator (Ultravent; Mallinckrodt). The generator will be driven with compressed air at 40 psi, generating 10 liters/min of aerosol. Using a series of one-way valves, nose clips, and mouth piece, the system will be closed; that is all gas, including aerosolized GSH will either be inspired or expired through a filter to collect all expired drug.

RESULT

Figure 5:
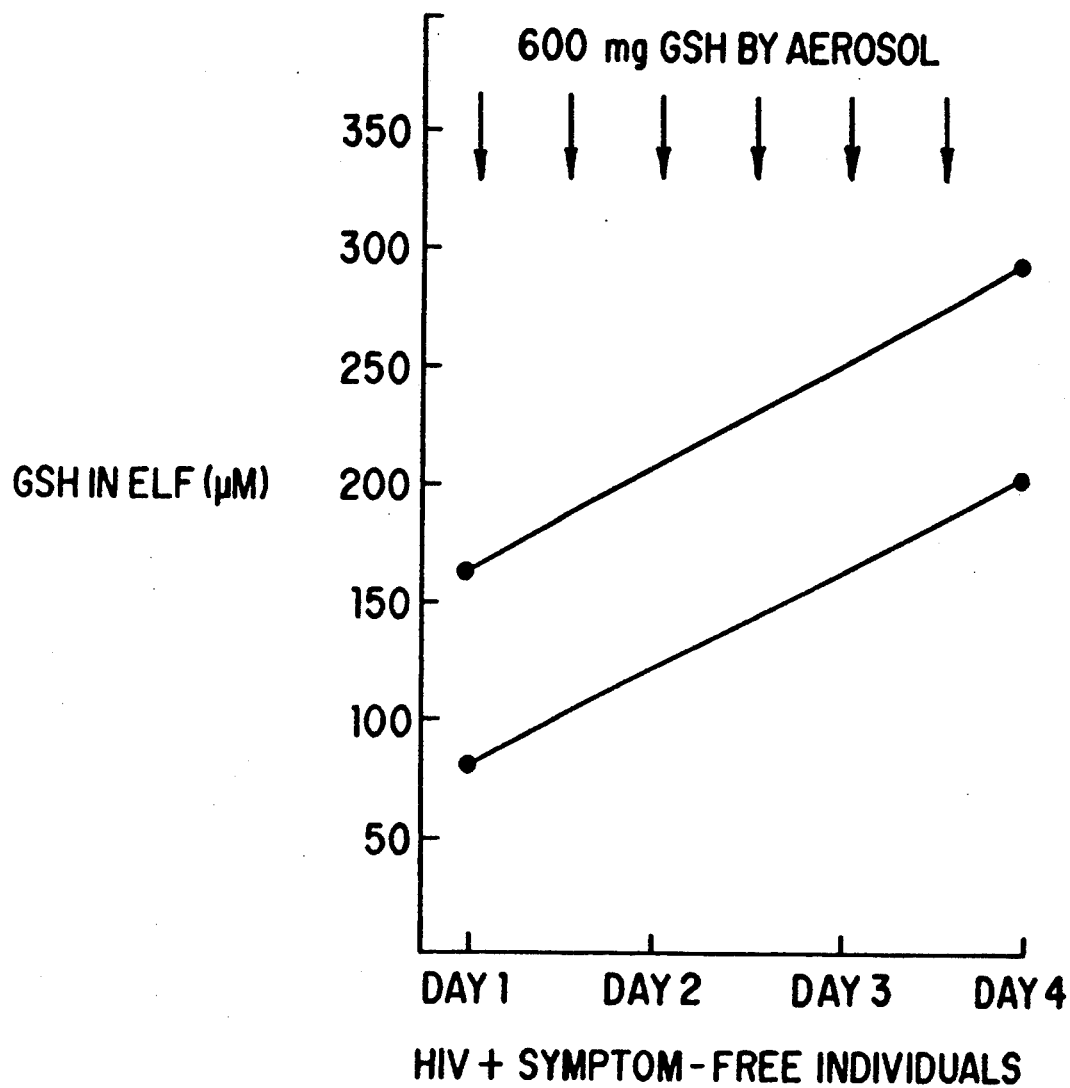
FIG. 5 shows the level of GSH in the lungs of two HIV-infected, non-symptomatic patients before GSH administration and one hour after administration of 600 mg GSH by aerosol twice daily for 3 days.

FIG. 5 shows the results of the aerosolization of glutathione to two individuals seropositive for the HIV virus (but asymptomatic, i.e., they are "pre-AIDS"). As shown in FIG. 5, these two individuals received 600 mg of glutathione aerosol twice daily for 3 days for a total of 6 doses. The lung epithelial lining fluid was assessed by bronchoalveolar lavage before any therapy and then 1 hour after the 6th dose following the same procedures as described herein supra. Both individuals started with glutathione levels in the lung fluid less than the normal range, but with therapy increased significantly, i.e., "correcting" the deficiency state. No adverse or toxic effects were observed in the treated patients.

In summary, it is clear from both the animal and the human studies that pulmonary ELF GSH level is significantly augmented by aerosolized administration of GSH.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. An effective amount of reduced Glutathione (GSH) in a pharmaceutically acceptable carrier, in the form of an aerosol suitable for administration by inhalation, for augmenting the GSH level in the lungs.

2. The aerosol of claim 1 comprising about 10 mg to about 2,500 mg of GSH in sterile, about 0.9% in terms of weight by volume, of sodium chloride solution, contained in a sterile pneumatic aerosol generator reservoir, so that an aerosol of said GSH is produced at the rate of about 8-12 liters per minute at about 30-50 psi of compressed air.

3. The aerosol of claim 2 produced at about 10 liters per minute at about 40 psi of the compressed air.

4. A method for augmenting GSH level in the lungs, comprising administering the aerosol of claim 1 through inhalation to the lungs.

5. A method for combating pulmonary dysfunction, disorder or disease where augmented level of GSH is deemed desirable, comprising administering the aerosol of claim 1 through inhalation to the lungs in an amount sufficient to augment GSH level in the lungs.

* * * * *